United States Patent [19]
Ohki et al.

[11] 3,932,382
[45] Jan. 13, 1976

[54] DIDEOXYBUTIROSIN DERIVATIVE

[75] Inventors: Eiji Ohki; Hiromichi Saeki; Shinichi Sugawara, all of Tokyo, Japan

[73] Assignee: Sankyo Company Limited, Japan

[22] Filed: Mar. 28, 1974

[21] Appl. No.: 455,943

[30] Foreign Application Priority Data
Apr. 11, 1973 Japan................................ 48-41175

[52] U.S. Cl. ....... 260/210 AB; 260/210 K; 424/180
[51] Int. Cl.² ........................................ C07H 15/22
[58] Field of Search.................... 260/210 AB, 210 K

[56] References Cited
UNITED STATES PATENTS
3,784,541   1/1974   Culbertson et al. .......... 260/210 AB

OTHER PUBLICATIONS

Umezawa et al. "Jour. of Antibiotics" Vol. 25, No. 10, 1972, pp. 613–615.

*Primary Examiner*—Johnnie R. Brown
*Attorney, Agent, or Firm*—Toren, McGeady and Stanger

[57] ABSTRACT

New derivative of butirosin A, 3', 4'-dideoxybutirosin A having not only broad antibacterial activities against gram-positive and -negative bacteria but also an activity against butirosin-resistant bacteria with a low toxicity. It is prepared from the corresponding 3', 4'-dideoxy-3'-eno derivative derived from butirosin A or a mixture of butirosins A and B by catalytic reduction.

3 Claims, No Drawings

DIDEOXYBUTIROSIN DERIVATIVE

This invention relates to a new derivative of antibiotic substance butirosin A and its pharmaceutically acceptable acid addition salts.

More particularly, it is concerned with 3',4'-dideoxybutirosin A having the formula

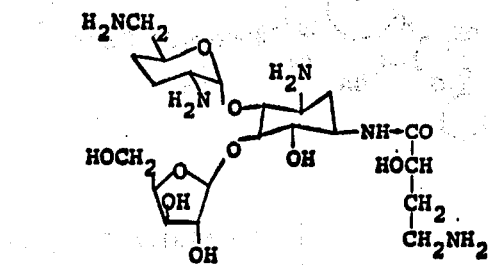

as well as its pharmaceutically acceptable acid addition salts.

The dideoxybutirosin A of this invention is a novel compound which is useful as a medicine, as it has not only broad antibacterial activities against gram-positive and -negative bacteria as butirosin has, but also an activity against butirosin -resistant bacteria. Moreover, the present compound surprisingly has a considerably low toxicity as compared with the prior similar aminoglycoside antibiotics.

It is, accordingly, a primary object of this invention to provide the new and valuable butirosin A derivative having the above-mentioned formula (I), and its acid addition salts.

Other objects and advantages of this invention will be apparent from the following disclosure.

The dideoxybutirosin A of this invention may be preferably administered through parenteral route, for example, by intravenous, intramuscular, subcutaneous or like injection in the same manner as done with common aminoglycoside antibiotic substances, but it may be orally administered, for example, with capsules, tablets and the like. The dosage may depend upon the body weight and the kind and severity of a disease, but a daily dose for adult is about 100 – 2000 mg., usually about 250 – 500 mg. in divided forms 2 – 4 times per day.

According to the process of this invention, the compound having the above-mentioned formula (I) can be obtained by catalytic reduction of a compound having the general formula

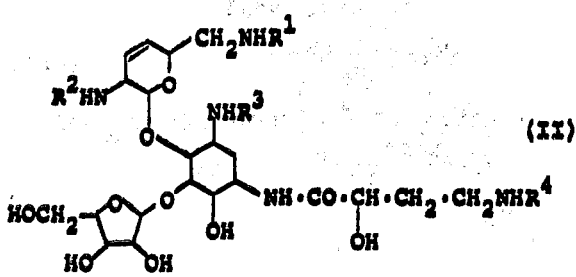

wherein $R^1$, $R^2$, $R^3$ and $R^4$ may be the same or different and each represents hydrogen atom or a group removable by reduction.

In the above general formula (II), the group, which is removable by reduction and represented by $R^1$, $R^2$, $R^3$ or $R^4$, means the group removable by catalytic reduction to form a free amino group and preferably may be given an aralkyloxycarbonyl group such as benzyloxycarbonyl, naphthylmethyloxycarbonyl, p-nitrobenzyloxycarbonyl and the like or allyloxycarbonyl group.

The process of this invention may be advantageously practiced in the same manner as done in common catalytic reduction. For instance, one may conduct the process by contacting the compound having the above general formula (II) with hydrogen in the presence of a catalyst in an appropriate solvent. As the solvent employed in the reaction, there is no particular limitation if a solvent does not participate with this reaction, but there may be given, in consideration of the solubilities of the starting compound and the final product, water; an alcohol such as methanol, ethanol or isopropanol; an ether such as dioxane or tetrahydrofuran, dimethylformamide and the like. An aqueous alcohol is particularly preferred. Where any of $R^1$ to $R^4$ is an aralkyloxycarbonyl group, the reaction may proceed more smoothly by conducting it with addition of an acid such as hydrochloric acid, hydrobromic acid or trifluoroacetic acid. As the catalyst employed in the reaction, there may be, without any particular limitation, employed those catalysts commonly utilizable for saturation of a double bond. For example, metal elements such as palladium, platinum, nickel, rhodium and the like, their oxides and catalysts of such metals adsorbed on carriers, e.g., carbon, barium carbonate, barium sulfate, silk yarn and the like, are mentioned. Usually and preferably is used palladium-carbon. The reaction may be usually effected at room temperature and under atmospheric pressure, but it may be done at any other temperature and pressure. It usually takes about several minutes to several hours to accomplish the reaction.

After completion of the reaction, the desired product may be recovered from the reaction mixture by conventional methods. For example, the catalyst is filtered off from the reaction mixutre, a weakly basic anion exchange resin is added to the filtrate to adjust its pH to 5–6, and, after filtration, the solvent is distilled off to give the end product. This product may be further purified by conventional methods such as ion exchange chromatography, if required.

The compound of the above general formula (II) which may be employed as a starting material in the process of this invention is novel and produced from butirosin A [H. W. Dion et al., Antimicrobial Agents and Chemotherapy, 2, 84 (1972)] or a mixture of butirosins A and B, for example, according to the method as shown below. In the following formulae, configurations of all bonds are the same as seen in butirosin A.

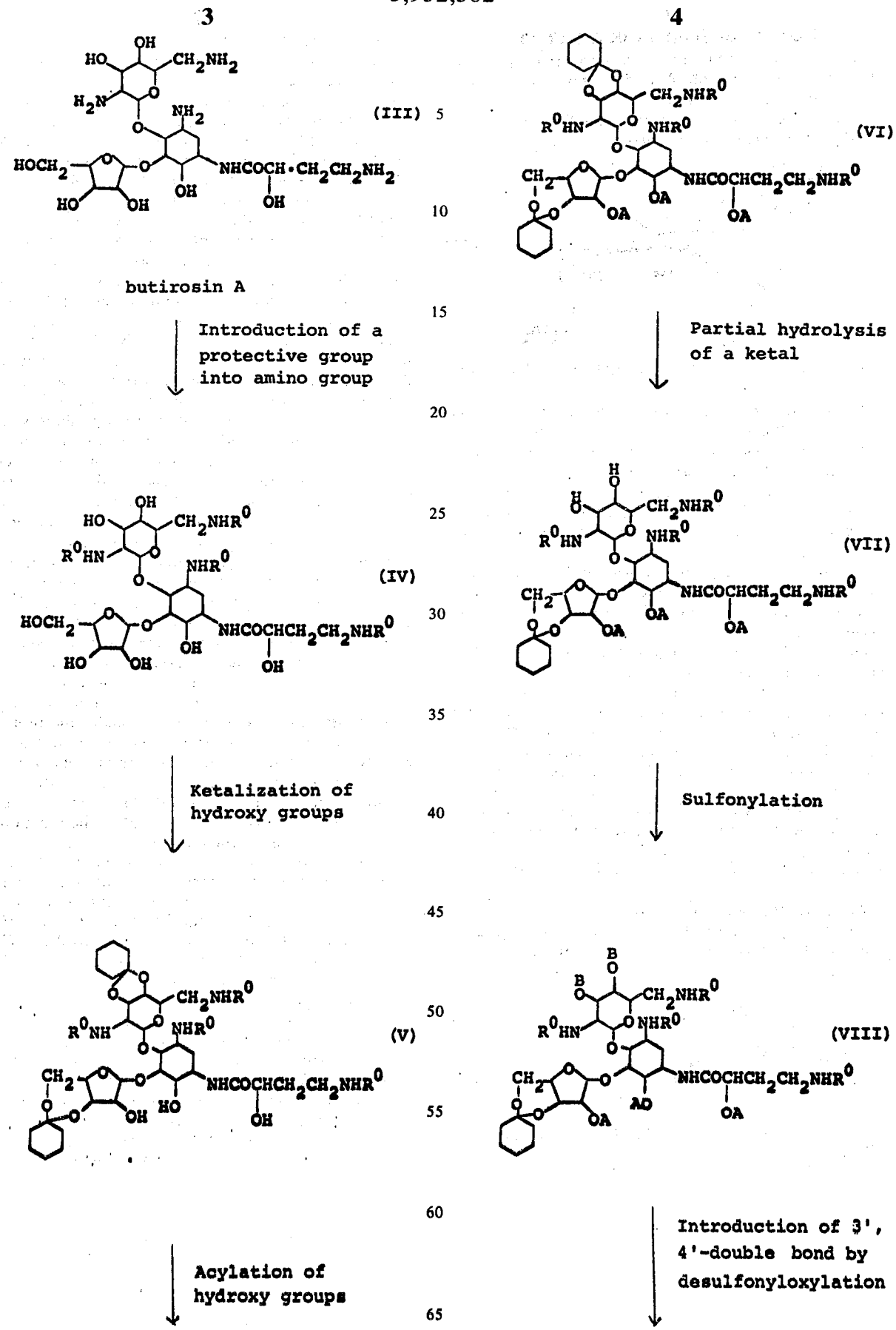

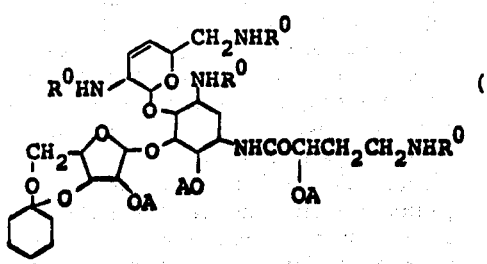

Deacylation of hydroxy groups

Hydrolysis of a ketal

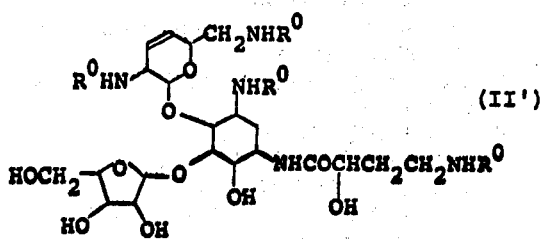

(wherein, R⁰ represents R¹ − R⁴ or an arylsulfonyl group such as tosyl, benzenesulfonyl, A represents an acyl group such as acetyl, propionyl, benzoyl and B represents a hydrocarbylsulfonyl group such as methanesulfonyl, toluenesulfonyl). Where R⁰ is an arylsulfonyl group or an allyloxycarbonyl group, treatment with liquid ammonia-metallic sodium gives the compound wherein R⁰ is hydrogen atom.

The antibacterial activities of the compound of this invention are given in the following Table I.

Table I

Minimum Inhibitory Concentration of 3',4'-Dideoxybutirosin A

| Microorganism | MIC (mcg/ml) |
|---|---|
| Bacillus subtilis P C I-219 | 0.1 |
| Staphylococcus aureus 209P | 0.1 |

Table I-continued

Minimum Inhibitory Concentration of 3',4'-Dideoxybutirosin A

| Microorganism | MIC (mcg/ml) |
|---|---|
| Staph. aureus 56 | 0.4 |
| Escherichia coli N I H J | 0.4 |
| E. coli 620* | 3.1 |
| E. coli 665* | 3.1 |
| Klebsiella 806 | 0.8 |
| Proteus vulgaris 025 | 0.8 |
| Salmonela enteritidis | 1.5 |
| Shigella flexneri 2a | 3.1 |
| Pseudomonas aeruginosa Scr. | 3.1 |
| Pseudomonas aeruginosa 1055* | 6.2 |

Mark *means butirosin-resistant bacteria
Medium : Heart-Infusion Agar

As illustrated in the above Table I, the 3', 4'-dideoxybutirosin A (I) of this invention shows outstanding activities against not only butirosin sensitive strains but also butirosin-resistant strains.

Table II

Protecting Effects of 3',4'-Dideoxybutirosin A in Mice $ED_{50}$ : mg./kg./dose (2 doses subcutaneously at 0 and 4 hours post-infection)

| Microorganism | 3',4'-Dideoxy butirosin A | Butirosin |
|---|---|---|
| E. coli 704-1 | 2.30 | 2.47 |
| E. coli 665* | 2.43 | 146.3 |

*Butirosin-resistant strain

Table III

Susceptibility of Clinical Isolates to 3',4'-Dideoxybutirosin A

| MIC mcg./ml. | >200 | 200 | 100 | 50 | 25 | 12.5 | 6.2 | 3.1 | 1.5 | 0.8 |
|---|---|---|---|---|---|---|---|---|---|---|
| E. coli (125 strains) | 0 | 0 | 2 | 2 | 15 | 100 | 6 | 0 | 0 | 0 |
| P. aeruginosa (102 strains) | 1 | 2 | 5 | 3 | 21 | 41 | 20 | 5 | 3 | 1 |

Table IV

Acute Toxicities of 3',4'-Dideoxybutirosin A

Mice : ddY strain, male, 20 ± 0.2 g.

| Route | Dose mg/kg. | Death incidence |
|---|---|---|
| i.v. | 500 | 1/2 |
| i.v. | 250 | 0/3 |
| s.c. | 2000 | 0/3 |

As described hereinabove, the pharmaceutically acceptable acid addition salts of the 3',4'-dideoxybutirosin A are contemplated to be within the purview of this invention and they may be easily formed in a conventional manner by the use of various inorganic or organic acid commonly used in the art for such purpose, for example, hydrochloric acid, hydrobromic acid, sulfuric acid, phosphoric acid, carbonic acid, acetic acid, succinic acid, citric acid, maleic acid or malic acid.

This invention will be more fully illustrated by the following Example and Referential Examples.

EXAMPLE

3',4'-Dideoxybutirosin A

In 4 ml. of methanol is dissolved 100 mg. of tetra-N-benzyloxycarbonyl-3',4'-dideoxy-3'-eno-butirosin A and 1.5 ml. of water, 0.1 ml. of 2N-hydrochloric acid and 0.2 g. of 10% palladium-carbon are added thereto. The mixture is stirred while hydrogen is being introduced. After about 2 hours, 0.1 ml. of 2N-hydrochliric acid is added and then introduction of hydrogen is continued for additional 1 hour. To the reaction mixture is added water and, after filtration, a weakly basic anion exchange resin, Amberlite IR-45 (OH$^-$ form) (Trade name) is added to the filtrate so that a pH of the solution may be adjusted to about 5 and filtered. The filtrate is concentrated at a bath temperature below 45°C. under a reduced pressure, the residue is dried in vacuo to give 61 mg. of colorless powdery substance. The substance is dissolved in water and adsorbed on a column of 16 ml. of a weakly acidic cation exchange resin, Amberlite CG-50 (NH$_4^+$ form) (Trade name) and eluted with 0.5N aqueous ammonia for a while to remove impurities and subsequently with 1N-aqueous ammonia. This eluate is concentrated at a bath temperature below 45°C. under a reduced pressure to remove the ammonia completely and then adjusted to pH of 5 by the addition of 0.1N-hydrochloric acid. The resulting solution is freeze-dried to give the hydrochloride of the desired product as colorless amorphous powders. The product is discolored to brown-colored at about 140°C. and decomposed at about 155°C. with foaming.

$[\alpha]_D^{23} + 19.2°$ (C = 1.8, H$_2$O)

Analysis for C$_{21}$H$_{41}$N$_5$O$_{10}$·4HCl·2H$_2$O
Calculated: C, 35.69; H, 6.99; N, 9.91; Cl, 20.07
Found: C, 35.22; H, 6.81; N, 10.23; Cl, 20.66

Following the substantially same procedure as set forth above except that carbon dioxide is employed instead of the 0.1N-hydrochloric acid in the neutralization step, there is obtained the carbonate of 3',4'-dideoxybutirosin A.

M.P. 130° – 145°C. (foaming at 168°C.)
$[\alpha]_D^{25} + 15.7°$ (C = 0.79, H$_2$O)

Analysis for C$_{21}$H$_{41}$N$_5$O$_{10}$·2H$_2$CO$_3$·2H$_2$O
Calculated: C, 40.40; H, 7.22; N, 10.24
Found: C, 40.51; H, 7.52; N, 10.58

REFERENTIAL EXAMPLE

Tetra-N-benzyloxycarbonyl-3',4'-dideoxy-3'-eno-butirosin A

1. Tetra-N-benzyloxycarbonylbutirosin (IVa)

In a mixture of 200 ml. of water and 80 ml. of methanol is dissolved 11.7 g. of butirosin disulfate dihydrate (a mixture of butirosin A and butirosin B, 4 : 1) and 8.0 g. of anhydrous sodium carbonate is added thereto. 10.5 ml. of benzyloxycarbonyl chloride is added dropwise thereto over 30 minutes, while stirred vigorously under ice-cooling. After completion of the dropwise-addition, 20 ml. of methanol is added and stirring is continued at room temperature for further 3 hours. The methanol is distilled off from the reaction mixture at a bath temperature below 45°C. under a reduced pressure and ice-water is added to separate out an oily substance. The aqueous layer is removed by decantation and ice-water is added thereby the oily substance is being washed. After standing, the aqueous layer is removed by decantation. After washing with water repeatedly according to the procedure mentioned just above, 50 ml. of ether is added and the washing with ether is conducted in the same manner as made in the above washing with water. After washing twice with ether, an oily substance is dissolved in methanol and filtered. The methanol is distilled off from the filtrate under a reduced pressure, 300 ml. of ether is added to the residue and then the mixture is allowed to stand in a refrigerator overnight. The supernatant is removed by decantation and the solvent completely distilled off from the residue under a reduced pressure to give 17.7 g. of crude product as colorless powder, which can be utilized in the subsequent step without further purification.

The crude product is dissolved in dioxane and adsorbed on a column using about 20 times volume of silica gel, which is then eluted with a mixture of methanol-chloroform (5 – 15 V/V % methanol). The solvent is distilled off under a reduced pressure and the residue is dissolved in a small amount of methanol. Precipitation with ether gives a pure product as powders.

IR spectrum $\nu$ cm$^{-1}$ (Nujol):
  1700, (a broad and strong absorption on CO of benzyloxycarbonyl group)
  1540, (a strong absorption on 2nd absorption of amido)

Analysis for C$_{53}$H$_{65}$N$_5$O$_{20}$·½H$_2$O
Calculated: C, 57.81; H, 6.04; N, 6.36
Found: C, 57.64; H, 5.94; N, 6.39

2. Tetra-N-benzyloxycarbonyl-3',4':3'',5''-di-O-cyclohexylidenebutirosin A (Va)

In 30 ml. of dry dimethylformamide is dissolved 10 g. of the (IVa) crude product obtained above and 6 ml. of 1,1-dimethoxycyclohexane and 0.35 g. of p-toluenesulfonic acid monohydrate are added. The resulting mixture is refluxed with stirring for 1.25 hours at a bath temperature of 35°C. under a reduced pressure (4 mmHg.). To the reaction mixture is added excess anhydrous potassium carbonate and stirring is made for 20 minutes followed by filtration. The solvent is distilled off from the filtrate at a bath temperature of 50°C. under a reduced pressure, the residue is dissolved in chloroform and the solution is adsorbed on a column using 200 g. of silica gel, which is then eluted with a mixture of methanol-chloroform (2 – 5 V/V % methanol). The product is confirmed by a thin layer chromatography. The solvent is distilled off from the eluate to give 6.5 g. of the desired compound of this step as powders.

NMR spectrum (60 MHz, CDCl$_3$):
  A broad signal is observed from the proton of the cyclohexylidene group (10 H) between $\delta$ 1.0 and $\delta$ 2.0.

Analysis for C$_{65}$H$_{81}$N$_5$O$_{20}$
Calculated: C, 62.34; H, 6.52; N, 5.59
Found: C, 61.99; H, 6.49; N, 5.31

The product thus obtained is hydrolyzed with hydrochloric acid and a paper chromatography for detection of a sugar [Toyo filter paper No. 51, ethyl acetatepyridine-water (8 : 2 : 1 and an upper phase of 3.6 : 1 : 1.15), color developed by aniline hydrogen phthalate] showed only xylose.

3. Tri-O-acetyl-tetra-N-benzyloxycarbonyl-3',4':3'',5''-di-0-cyclohexyliidenebutirosin A (VIa)

In 20 ml. of pyridine is dissolved 3.7 g. of the product (Va) and 8 ml. of acetic anhydride is added. The mixture thus obtained is left at room temperature overnight. The reaction mixture is poured into ice-water and, after stirring well, the mixture is allowed to stand for 30 minutes. The supernatant is removed by decantation and oily residue is dissolved in chloroform. The solution thus obtained is washed in sequence with 2N-hydrochloric acid, water, saturated aqueous sodium bicarbonate and water and then dried over anhydrous magnesium sulfate. The solvent is distilled off from the solution to give the desired compound of this step as colorless powders.

Analysis for $C_{71}H_{87}N_5O_{23}$
Calculated: C, 61.86; H, 6.39; N, 5.08
Found: C, 61.27; H, 6.34; N, 4.99

4. Tri-o-acetyl-tetra-N-benzyloxycarbonyl-3'',5''-O-cyclohexylidene-3',4'-di-o-methanesulfonylbutirosin A (VIIIa)

In 40 ml. of acetic acid is dissolved 4.2 g. of the product (VIa), 12 ml. of water is added and the mixture is left at room temperature for 2 hours. The reaction mixture is ice-cooled and an aqueous 1N-sodium hydroxide solution is added in a sufficient amount to neutralize the half of the acetic acid followed by extraction with chloroform. The extract is washed with a cold aqueous 1N-sodium hydroxide solution until the acetic acid in the extract is completely removed. After washing with water, it is dried over anhydrous magnesium sulfate. The solvent is distilled off from the solution to give 3.6 g. of crude product of tri-o-acetyltetra-N-benzyloxycarbonyl-3'', 5''-0-cyclohexylidenebutirosin A (VIIa). The so obtained crude product is dissolved in 30 ml. of pyridine and 7.2 ml. of methanesulfonyl chloride is added under ice-cooling and allowed to stand at room temperature for 1 hour. A little amount of water is added to the reaction mixture to decompose the unreacted chloride and then the mixture is made alkaline with a saturated aqueous sodium bicarbonate solution. Thereafter, complete precipitation is made by the addition of ice-water. The supernatant is removed by decantation and the residue is washed with water. The whole aqueous phase is extracted with a little amount of chloroform. The extract is combined with a solution of the residue in chloroform, the mixture is washed in sequence with 2N-hydrochloric acid, water, a saturated aqueous sodium bicarbonate solution and water and then dried over anhydrous magnesium sulfate. The solvent is distilled off from the solution to give 3.6 g. of the crude desired compound of this step as yellow powders. A solution of the so obtained powder in chloroform is adsorbed on a column using 72 g. of silica gel, which is eluted with chloroform for a while and subsequently with a mixture of methanolchloroform (1–2 V/V % methanol). From the eluate with the mixture is distilled off the solvent to give 2.6 g. of the pure product as colorless powders.

NMR spectrum (60 MHz, $CDCl_3$):
Absorption on the methyl of methanesulfonate at $\delta$ 3.07 (S) and $\delta$2.81 (S), one absorption on the methyl of acetyl at $\delta$2.13 (S), and two absorptions on the methyl of acetyl at 2.06 (S)

Analysis for $C_{66}H_{83}O_{27}N_5S_2$
Calculated: C, 54.95; H, 5.80; N, 4.86; S, 4.45
Found: C, 55.41; H, 5.80; N, 4.80; S, 4.40

5. Tetra-N-benzyloxycarbonyl-3',4'-dideoxy-3'-enobutirosin A (IIa)

In 8 ml. of dry dimethylformamide is dissolved 843 mg. of the product (VIIIa) and 2.3 g. of zinc powder is added thereto. The mixture is heated at 95° – 100°C. and 4.5 g. of sodium iodide is added with vigorous stirring. Heating is continued for 1.5 hours followed by cooling. To the reaction mixture is added about 6 times volume of chloroform and then the resulting mixture is filtered. The filtrate is washed with a saturated aqueous solution of sodium hydrosulfite and dried over anhydrous magnesium sulfate. The solvent is distilled off from the solution under a reduced pressure to give 0.8 g. of a yellow oily substance. The oily substance is dissolved in 6 ml. of methanol and 0.3 ml. of a methanolic solution of 2N-sodium methoxide is added to the resulting mixture. The mixture is left at room temperature for 15 minutes. Dilution with chloroform is done under ice-cooling, followed by washing with aqueous sodium chloride and drying over magnesium sulfate. The solvent is distilled off from the solution to give 0.7 g. of crude tetra-N-benzyloxycarbonyl-3'',5''-cyclohexylidene-3',4'-dideoxy-3'-eno-butirosin A (IXa) as an oily substance. This crude product is dissolved in chloroform and the solution is adsorbed on a column using 15 g. of silica gel, which is then eluted with chloroform for a while and subsequently with a mixture of methanol-chloroform (2 – 5 V/V % methanol). From the eluate by the mixture is distilled off the solvent to give 344 mg. of the pure (IXa) product. This product is dissolved in a mixture of 2 ml. of acetic acid and 0.7 ml. of water, the solution is heated on a steam bath for 10 minutes and concentrated at a bath temperature below 60°C. under a reduced pressure. The residue is dissolved in a little amount of ethyl acetate and ether is added to separate tetra-N-benzyloxycarbonyl-3',4'-dideoxy-3'-eno-butirosin A, which is then recovered by filtration and dried. Yield, 259 mg.

NMR spectrum (60MHz, pyridine-$d_5$):
$\delta$5.83 (br. s) 2H and no signal on the methyl is observed.

Analysis for $C_{53}H_{63}N_5O_{18}\cdot1\frac{1}{2}H_2O$
Calculated: C, 58.66; H, 6.13; N, 6.45
Found: C, 58.51; H, 5.94; N, 6.51

What is claimed is:
1. 3', 4'-Dideoxybutirosin A having the formula

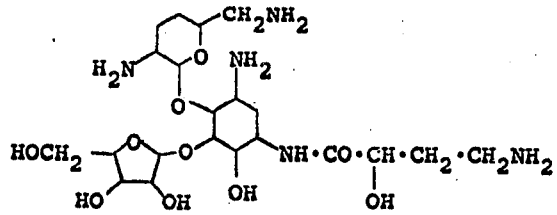

and its pharmaceutically acceptable acid addition salt.
2. 3', 4'-Dideoxybutirosin A hydrochloride.
3. 3', 4'-Dideoxybutirosin A carbonate.

* * * * *